(12) United States Patent
Nishizawa et al.

(10) Patent No.: US 6,479,657 B1
(45) Date of Patent: *Nov. 12, 2002

(54) CRYSTALLINE 1-KESTOSE AND PROCESS FOR PREPARING THE SAME

(75) Inventors: Koji Nishizawa; Hitoshi Matsumoto; Hirofumi Nakamura; Takashi Kawakami; Yuko Nakada; Masao Hirayama; Takashi Adachi, all of Saitama-ken (JP)

(73) Assignee: Meiji Seika Kaisha, Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/091,182

(22) PCT Filed: Dec. 11, 1996

(86) PCT No.: PCT/JP96/03618
§ 371 (c)(1),
(2), (4) Date: Sep. 29, 1998

(87) PCT Pub. No.: WO97/21718
PCT Pub. Date: Jun. 19, 1997

(30) Foreign Application Priority Data

Dec. 11, 1995 (JP) .............................. 7-321951
Mar. 21, 1996 (JP) .............................. 8-64682
Mar. 21, 1996 (JP) .............................. 8-77534
Mar. 29, 1996 (JP) .............................. 8-77539

(51) Int. Cl.$^7$ .............................. C07H 1/06; C07H 3/06; C12P 19/44
(52) U.S. Cl. ............... 536/124; 536/123.1; 536/123.12; 435/74; 435/101; 435/105; 435/124; 435/127
(58) Field of Search .............................. 536/124, 123.1, 536/123.12; 435/74, 101, 105, 124, 127

(56) References Cited

U.S. PATENT DOCUMENTS 5,463,038 A * 10/1995 Hidano et al. ............... 536/124

FOREIGN PATENT DOCUMENTS

EP 0 474 046 3/1992
JP 5-70415 10/1993

OTHER PUBLICATIONS

Takeda et al., Production of 1–Kestose . . . , J. of Fermentation and Bioeng., vol. 77(4), pp. 386–389, 1994.*
Letter to European Patent Office, in response to Office Action for EP app. 91114080.4–2399, 1994.*
R. A. McGinnis, Beet–Sugar Technology (Third Edition), p. 466, 1982.
Hiroyuki Takeda et al., "Method for Production of 1–Kestose Crystal", Proceedings of the Research Society of Japan Sugar Refineries' Technologists, vol. 40, pp. 17–21, Nov. 1992.
Hiroyuki Takeda et al., "Production of 1–Kestose by *Scopulariopsis brevicaulis*", Journal of Fermentation and Bioengineering, vol. 77, No. 4, pp. 386–389, 1994.
George P. Meade, Cane Sugar Handbook: A Manual for Cane Sugar Manufacturers and Their Chemists, (9th edition), pp. 192–193, (1963).
Eijiro Hamaguti and Yosito Sakurai, Sugar Handbook, pp. 49, 191–192 (1964).
Hiroyuki Takeda et al., "The Industrial Crystallization Method for Fructosylxyloside Produced by *Scopulariopsis brevicaulis*", Journal of Fermentation and Bioengineering, vol. 80, No. 5, pp. 492–498, (1995).
Y. Hatayama et al., "The Purification of β–Fructofuranosidase from *Scopulariopsis brevicaulis* N–01", Abstracts of publications of the Japan Society for Bioscience, Biotechnology and Agrochemistry, p. 297, (Mar. 1996).
H. Hidaka and M. Hirayama, "Fructooligosaccharide–producing Enzymes from Microorganisms and Plants", BioScience Laboratories, Meiji Seika Kaisha, Ltd., vol. 23, No. 9, pp. 600–605 (1985).
Tomotari Mitsuoka, Intestinal Flora and Edible Factor, Japan Scientific Societies, pp. 39–66 (1984).
Hidemasa Hidaka et al., "Effects of Fructooligosaccharides on Intestinal Flora and Human Health", Bifidobacteria Microflora, vol. 5, pp. 37–50, (1986).
Letter to European Patent Office dated Aug. 24, 1993, in response to the Official Action of Feb. 18, 1993 for European Patent Application 91114080.4–2399.

* cited by examiner

Primary Examiner—James O. Wilson
Assistant Examiner—Howard Owens
(74) Attorney, Agent, or Firm—Wenderoth, Lind & Ponack, L.L.P.

(57) ABSTRACT

A process for producing crystal 1-kestose wherein granular crystal 1-kestose in the form of large crystals can be produced at a high yield is disclosed. A highly pure solution of 1-kestose is concentrated to a Brix of 75 or higher; either seed crystals are added, or the solution is vacuum-concentrated to generate microcrystals for use as nuclei; then, a crystal growing step by vacuum-concentration and a microcrystal dissolving step for redissolving microcrystals which have formed in the concentrate are repeated at least twice each. Alternatively, a highly pure solution of 1-kestose is concentrated to a Brix of 80 or higher; either seed crystals are added, or the solution is allowed to initiate crystallization; after crystals are allowed to grow, a cooling step where the temperature is lowered by 5° C. to 20° C. from the previous step and a crystal growing step where the concentrate is maintained at the temperature to allow the crystals to grow are repeated at least twice each. Also, an enzyme for producing 1-kestose efficiently from sucrose is disclosed.

16 Claims, No Drawings

CRYSTALLINE 1-KESTOSE AND PROCESS FOR PREPARING THE SAME

BACKGROUND OF THE INVENTION

1. Field of the Invention

The present invention relates to a process for producing crystal 1-kestose, specifically a process for producing large crystal grains of crystal 1-kestose by vacuum crystallization or cold crystallization at a high yield. The present invention also relates to an enzyme for efficiently producing 1-kestose, and a process for producing crystal 1-kestose using said enzyme.

2. Description of the Related Art

The molecular structure of 1-kestose, a type of trisaccharide, is the same as that of sucrose except that the fructose half of 1-kestose is coupled with another fructose at position 1 via a β-2,1 bond. Fructooligosaccharides are characterized by little cariosity, indigestibility to biological digestive enzymes, and the specific facilitation of the growth of Bifidobacterium in the intestines, as demonstrated by some of the present inventors of the present invention (Japanese Patent Publication No. 53834/1984). It is believed that 1-kestose, which is a component of fructooligosaccharides, also has the same characteristics.

Commercially available crystalline oligosaccharides have been limited to raffinose, which has small crystal grain sizes of about 0.1 to 0.3 mm lengthwise. The currently most well-known crystalline sugar, sucrose, is produced mostly as granulated sugar, which is composed primarily of large crystals of about 0.25 to 1 mm, and soft sugar, which is a mixture of large and medium crystals of about 0.1 to 0.5 mm. In oligosaccharides, large grains are also favored for high utility.

Although both 1-kestose and sucrose have columnar crystals, the crystals of 1-kestose are more rectangular than the almost cubic crystals of sucrose. Therefore, 1-kestose should have larger crystals than sucrose in order to show physical properties similar to those of granulated sugar.

In a previously disclosed method for producing crystal 1-kestose, aqueous solution of 1-kestose of Brix 85 or higher and a purity of 70% or higher is heated to a temperature of 80° C. or higher; a suspension of microcrystals is added to the solution; the temperature is lowered to 65 to 75° C. to deposit crystals; and, while the temperature is maintained at 60 to 80° C., the deposited crystal 1-kestose is recovered (Japanese Patent Publication No. 70075/1994).

This method has a disadvantage in that the yield of crystals is low at about 30 to 40% because the concentration and purity of the crystallizing solution drop as crystals deposit. Further, this method unavoidably involves the deposition of microcrystals with increasing the viscosity of the solution. Thus, the solution should be heated during the recovery of crystals. Further, the grain sizes of the obtained crystals are not uniform and generally small.

On the other hand, 1-kestose may be produced from sucrose, making use of the activity of fructose transferase. In one of such known methods, sucrose solution adjusted to a concentration of 50% or higher is allowed to react at pH 4.0 to 7.0 in the presence of an enzyme having fructose transferase activity which is derived from an Asperaillus or Fusarium microorganism (Japanese Patent Publication No. 62184/1988). In another known method, an enzyme having fructose transferase activity derived from an AsTeraillus microorganism is allowed to react at pH 4.0 to 7.0, a temperature of 25 to 65° C., and a sucrose concentration of 20 to 70% (Japanese Patent Laid-Open Publication No. 268190/1986).

However, these methods are aimed primarily to obtain a mixture of a trisaccharide (1-kestose), a tetrasaccharide (nystose), and a pentasaccharide (fructosyl nystose), i.e., fructooligosaccharides, from sucrose. The rates of conversion from sucrose to 1-kestose in this method are only 36 to 41% at maximum (refer to Table 3 in Japanese Patent Publication No. 62184/1988, and Examples in Japanese Patent Laid-Open Publication No. 268190/1986). Also, in these methods, 11 to 23% of nystose is produced along with 1-kestose, leaving 11 to 23% of non-reacted sucrose, while 13 to 32% of monosaccharides such as fructose or glucose are produced as byproducts (ibid.).

It should be noted that the presence of monosaccharides, sucrose, and nystose is disadvantageous for the following reason: In the two-component simulated-moving bed chromatographic separation, which is used generally for producing isomerized sugar, etc., a solution containing two or more sugars of different molecular weights is divided into two fractions according to the difference in their molecular weights. If this method is used to obtain 1-kestose of high purity from a solution containing 1-kestose, the solution should be either (1) divided into two fractions, i.e., a fraction containing sugars with lower molecular weights than 1-kestose, and one containing those with molecular weights equal to or higher than that of 1-kestose, including 1-kestose; or (2) divided into two fractions, i.e., a fraction containing sugars with higher molecular weights than 1-kestose, and one containing those with molecular weights equal to or lower than that of 1-kestose, including 1-kestose. In the former case, for example, as the fraction contains sugars of higher molecular weights than that of 1-kestose, the purity of 1-kestose in the fraction is inevitably low depending on the content of such sugars. When the solution contains high contents of sugars whose molecular weights are higher than that of 1-kestose, e.g., nystose, with the two-component simulated-moving bed chromatographic separation, two or more steps of operations are required, such as a second chromatographic separation of the resultant fraction, in order to obtain 1-kestose solution at a high purity (e.g., 80% or higher), which is necessary for crystallization. In the latter case, the process has the same disadvantage when the contents of monosaccharides and sucrose are high. Therefore, a need exists for a method using enzymatic reactions in which the production of monosaccharides, sucrose, nystose, etc., is reduced, that is, a method in which 1-kestose can be selectively produced, and the conditions and a novel enzyme for this method.

Among Penicillium microorganisms, it has been suggested that *Penicillium frequentans* has an enzyme having fructose transferase activity (Japanese Patent Laid-Open Publication No. 293494/1992). However, this report only states that the microorganism produces fructose transferase, does not mention the rate of conversion to 1-kestose.

A method for selectively producing 1-kestose using a Scopulariopsis microorganism that produces 1-kestose in the presence of sucrose while consuming glucose has been reported (Japanese Patent Publication No. 47197/1993, Japanese Patent Publication No. 41600/1992). After the microorganism is incubated in a medium containing sucrose to produce 1-kestose, 1-kestose is recovered from the culture. According to the publication, the rate of conversion from sucrose to 1-kestose is as high as 60%. However, since the method uses the whole fungus body, the total sugar concentration in the culture, i.e., the sucrose concentration at the beginning of incubation, should be as low as about 15%. In addition, high contents of proteins and other impurities should be removed during purification.

Thus, methods for producing 1-kestose more selectively, particularly a novel enzyme and novel conditions for reaction, are solicited.

SUMMARY OF THE INVENTION

Inventors have now found that the viscosity of the fraction can be made low enough to enable the separation of crystals as solids from the solution at room temperature without heating the solution, by a controlled concentration procedure and temperature control based on what is called vacuum crystallization or cold crystallization. It has also be found that larger crystals of 1-kestose are obtained at a high yield. The inventors have also found certain microorganisms produce enzymes which efficiently produce 1-kestose. The present invention is based on these findings.

Thus, the object of the present invention is to provide a process for producing crystal 1-kestose wherein crystal 1-kestose is obtained at a high yield by the separation of solid from liquid at room temperature. Another object of the present invention is to provide a process for producing crystal 1-kestose wherein large crystals of crystal 1-kestose, preferably in a granular form, are obtained.

Still another object of the present invention is to provide large crystals of 1-kestose in a granular form.

According to the first aspect of the present invention, there is provided a process for producing crystal 1-kestose comprising the steps of:

(a) concentrating a highly pure 1-kestose solution having 80% or more of 1-kestose to a Brix of 75 or higher, adding seed crystals, and then heating the resultant concentrate to 60° C. or higher to allow crystals to grow, (b) as a crystal growing step, concentrating the concentrate under a reduced pressure to allow crystals to grow, and (c) as a microcrystal dissolving step following the crystal growing step, heating the concentrate to redissolve microcrystals which have been generated in the concentrate and, if the microcrystals fail to redissolve completely, adding water to the concentrate to dissolve the microcrystals, followed by repeating at least once each of the (b) crystal growing step and the (c) microcrystal dissolving step, and recovering crystal 1-kestose.

In addition there is provided a modified process of that according to the first aspect of the present invention comprising the steps of:

instead of steps (a) and (b) above, (a') concentrating a highly pure 1-kestose solution having 80% or more of 1-kestose to a Brix of 75 or higher, and heating the resultant concentrate to 60° C. or higher, and (b') concentrating the concentrate under a reduced pressure to lower the temperature of the concentrate and to initiate crystallization and allow the resultant crystals to grow, followed by the (c) microcrystal dissolving step as defined above, then by repeating at least once each of the (b) crystal growing step and the (c) microcrystal dissolving step as defined above, and recovering crystal 1-kestose.

According to the second aspect of the present invention, there is provided a process for producing crystal 1-kestose comprising the steps of:

(α) concentrating a highly pure 1-kestose solution having 80% or more of 1-kestose to a Brix of 80 or higher, heating the solution to 70 to 95° C., adding seed crystals, and maintaining the resultant concentrate in the temperature range to allow the crystals to grow, (β) as a succeeding cooling step, cooling the concentrate by 5 to 20° C. from the temperature in the previous step, and (γ) as a crystal growing step, maintaining the concentrate at the lowered temperature of the cooling step above to allow the crystals to grow, followed by repeating at least once each of the (β) cooling step and the (γ) crystal growing step, lowering the temperature to 20 to 60° C., and recovering crystal 1-kestose.

In addition, there is provided a modified process of that according to the second aspect of the present invention comprising the steps of:

instead of step (α) above, (α') concentrating a highly pure 1-kestose solution having 80% or more of 1-kestose to a Brix of 80 or higher, maintaining the temperature of the solution in the range of 50 to 60° C. to initiate crystallization, and then maintaining the resultant crystals at 70 to 95° C. to grow, followed by repeating at least once each of the (β) cooling step and the (γ) crystal growing step, lowering the temperature to 20 to 60° C., and recovering crystal 1-kestose.

According to the present invention, there is also provided a crystal 1-kestose in the form of columnar crystal having a length of 0.3 mm or longer (preferably 0.3 to 2 mm) and a purity of 95% or higher.

Further, according to the third aspect of the present invention, there is provided a process for producing crystal 1-kestose comprising the steps of:

(i) either of (1) allowing an enzyme having fructose transferase activity derived from an Aspergillus microorganism to react on a sucrose solution to produce 1-kestose accounting for 43 wt % or more of the resultant sugars, (2) allowing an enzyme having fructose transferase activity derived from a Penicillium microorganism to react on a sucrose solution to produce 1-kestose accounting for 46 wt % or more of the resultant sugars, or (3) allowing an enzyme having fructose transferase activity derived from a Scopulariopsis microorganism to react on a sucrose solution to produce 1-kestose accounting for 53 wt % or more of the resultant sugars;

(ii) isolating from 1-kestose obtained in step (i) a fraction having a purity of 80% or higher by chromatographic separation; and (iii) crystallizing 1-kestose fraction obtained in step (ii) to produce crystal 1-kestose in the form of columnar crystal having a length of 0.3 mm or longer and a purity of 95% or higher.

DESCRIPTION OF THE PREFERRED EMBODIMENTS

Process of the First and Second Aspects of the Present Invention

Crystallizing Sample

Both in the first and second aspects of the present invention, a crystallizing sample containing a highly pure 1-kestose is used as a starting material. A higher 1-kestose purity would be more advantageous, preferably 80% or higher in the process according to the present invention, and more preferably 90% or higher. The purity of 1-kestose herein refers to the content of 1-kestose expressed as the weight percentage of the sugar content in the crystallizing sample.

To prepare a crystallizing sample of 1-kestose, a sugar source containing 1-kestose is either prepared or obtained, and purified to increase its purity of 1-kestose. A sugar source containing 1-kestose may be prepared, for example, by allowing fructose transferase derived from a plant, a microorganism, etc., to react on sucrose or other substrate; by incubating a microorganism in a medium containing sucrose or other sugar; or from various commercially available mixtures of fructooligosaccharides by standard techniques such as chromatographic separation or membrane separation, or Steffen process, in which lime is used to precipitate impurities.

According to the preferred embodiment of the present invention, the proportion of nystose in the sugar content except 1-kestose in the crystallizing sample of 1-kestose should be minimal. Inventors have found that the nystose content in the crystallizing sample should be lower to obtain larger 1-kestose crystals. More specifically, it has been demonstrated that nystose, if exists, inhibits the crystallization of 1-kestose. The preferable nystose content is 10 wt % or less of 1-kestose.

This finding applies not only to the processes according to the first and second modes the present invention, but to previously known processes for producing 1-kestose as well.

Process of the First Aspect of the Present Invention

In the process according to the first aspect of the present invention, the crystallizing sample is first concentrated to a Brix of 75 or higher, preferably 80 to 85. Concentration may be performed by heating or decompression. Then, seed crystals are added to the concentrate. The preferable quantity of the seed crystals is 1 wt % or less of the solids content in the concentrate. After the seed crystals are added, the concentrate is allowed to continue to crystallize with the seed crystals as nuclei. It is preferable that the temperature of the concentrate be maintained at 60° C. or higher for about 0.5 to 6 hours, more preferably at 70 to 95° C. for 1 to 3 hours.

In another preferred embodiment of the present invention, crystal nuclei may be formed without adding seed crystals unlike the above procedure. The concentrate may be concentrated under a reduced pressure at a temperature of 60° C. or higher to deposit microcrystals, then allowed to continue to crystallize under the conditions above described with the microcrystals as nuclei. It is preferable that microcrystals be formed in the range of 10 to 160 mmHg in absolute pressure and 30 to 70° C. in temperature, more preferably in the range of 40 to 120 mmHg in absolute pressure and 50 to 60° C. in temperature.

After the concentrate is allowed to continue to crystallize as describe above, it is concentrated under a reduced pressure, preferably at an absolute pressure of 40 to 200 mmHg for 10 to 60 minutes, more preferably at an absolute pressure of 60 to 120 mmHg for 30 to 60 minutes. Through the concentration procedure, the temperature of the concentrate drops to 40 to 70° C., facilitating the growth of crystals (crystal growing step).

Following the crystal growing step, the concentrate is subjected to the microcrystal dissolving step described below. While the growth of 1-kestose crystals is observed as a result of vacuum concentration, the concentration procedure generally produces 1-kestose microcrystals as well. The microcrystals are redissolved by heating the concentrate preferably at 70° C. to 95° C., more preferably at 75 to 85° C., and maintaining the temperature for 0.5 to 6 hours, preferably 1 to 2 hours. If heating fails to redissolve the microcrystals completely, water is added to redissolve preferably the entire microcrystals.

In the process according to the first aspect, the microcrystal dissolving step is followed by the repetition of at least once each of the same crystal growing step and microcrystal dissolving step as described above. In particular, after the concentrate is maintained preferably at an absolute pressure of 40 to 200 mmHg for 10 to 60 minutes to allow the crystals to grow, the resultant microcrystals are redissolved by heating the concentrate preferably at 70° C. to 95° C. and maintaining the temperature for 0.5 to 6 hours. If the heating fails to redissolve the microcrystals completely, water is added to redissolve preferably the entire microcrystals.

The crystals of 1-kestose are allowed to grow sufficiently to a desired grain size in these steps. The obtained crystals may be isolated and recovered by standard techniques (e.g., by centrifugation). The preferred embodiment of the present invention has a significant advantage that, after crystallization is over, the concentrate, in which the crystals of 1-kestose have been allowed to grow sufficiently to a granular form, has a viscosity low enough to enable the recovery of the crystals without heating the solution. After recovery, the crystals may be dried as necessary to finally make crystal 1-kestose.

According to the first aspect of the present invention, 1-kestose is obtained at a yield as high as 50 to 60%.

According to the preferred embodiment of the present invention, crystal 1-kestose in the form of columnar crystals having lengths of 0.3 mm or longer (preferably 0.3 to 2 mm, more preferably 0.5 to 1.2 mm) and a purity of 95% or higher can be obtained. Specifically, by controlling the Brix to about 75 to 85, preferably about 79 to 83, in the crystal growing step described above, generation of microcrystals in the concentrate is inhibited, thereby facilitating the growth of crystals, to efficiently produce the large grains of crystal 1-kestose as described above.

In addition, in the method of the first aspect of the present invention, the crystallizing sample may be replenished to make up for the loss in volume caused in the crystal growing step above, after the crystal growing step and before the microcrystal dissolving step, or after the microcrystal dissolving step and before the second crystal growing step. This replenishment would help increase the volume processed per operation and, at the same time, maintain the high purity of 1-kestose in the solution, which may otherwise drop as crystallization proceed thereby, enabling crystallization to take place at a consistently high 1-kestose purity.

Crystal 1-kestose may be prepared in continuous processes by repeating the same procedure as described above or carrying out the procedure according to the second aspect as described below on the sugar solution containing 1-kestose from which crystal 1-kestose has been recovered. Alternatively, the same procedure as described above or the procedure according to the second aspect as described below may be repeated on the sugar solution containing 1-kestose from which crystal 1-kestose has been recovered after, as necessary, replenishing the solution with fresh crystallizing sample. These continuous procedures of crystallization would help further increase the yield of 1-kestose crystal, in some cases, to a total yield as high as 80% or higher.

Process of the Second Aspect of the Present Invention

In the process according to the second aspect of the present invention, the crystallizing sample is first concentrated to a Brix of 80 or higher, preferably 83 to 88. Concentration may be performed by heating or decompression. Then, while the concentrate is maintained at a temperature of 70 to 95° C., seed crystals are added to the concentrate. The preferable quantity of the seed crystals is 1 wt % or less of the solids content in the concentrate.

In another preferred embodiment of the present invention, crystal nuclei can be formed, without adding seed crystals unlike the above procedure. Interestingly, inventors have found that microcrystals, which function as crystal nuclei, can be formed efficiently by heating the concentrate, which has been concentrated to a Brix of 80 or higher, from around room temperature (about 25° C.) to 50 to 60° C., and that the number and size of the microcrystals can be controlled by regulating the rate of heating. Higher rate of heating from room temperature to the temperature range specified above would result in a smaller number of microcrystals as crystal nuclei, thus resulting in large crystals being formed. Furthermore, lower rate of heating would result in a greater number of microcrystals as crystal nuclei, thus resulting in small crystals.

After seed crystals are added or microcrystals which function as crystal nuclei are formed as described above, the concentrate is maintained at 70 to 95° C., preferably at 75 to 85° C., for 30 minutes to 6 hours to allow the crystals to grow.

In the next cooling step of this process, the concentrate is cooled to lower its temperature by 5 to 20° C., preferably by about 10° C., from the previous step. Then, the concentrate is maintained hot at the temperature for 30 minutes to 6 hours to allow the crystals to grow in a subsequent crystal growing step.

In this process, the cooling step and the crystal growing step are followed by the repetition of at least once each of the same cooling step and crystal growing step. In other words, the temperature of the concentrate is lowered from the previous step by 5 to 20° C., preferably by about 10° C., then maintained high at the same temperature for 30 minutes to 6 hours to allow the crystals to grow.

If a large amount of microcrystals have formed during crystallization, it is recommended that the solution temperature be increased preferably by about 10 to 20° C. from that when microcrystals formed, in order to redissolve the microcrystals. Then the cooling step and the crystal growing step are carried out again.

The cooling step and the crystal growing step are repeated until the temperature of the crystallizing solution is 20 to 60° C., preferably about 40 to 50° C.

The crystals of 1-kestose are allowed to grow sufficiently to a desired grain size in these steps. The obtained crystals may be isolated and recovered by standard techniques (e.g., by centrifugation). The preferred embodiment of the present invention has a significant advantage as does the process of the first aspect of the present invention. After crystallization is over, the concentrate containing the crystals of 1-kestose which have been allowed to grow sufficiently to a granular form, has a viscosity low enough to enable the recovery of crystals without heating the solution. After recovery, the crystals may be dried as necessary to finally make crystal 1-kestose.

According to the second aspect of the present invention, 1-kestose is obtained at a yield of 40% or higher, or as high as 43 to 55% in a preferred mode.

According to the preferred embodiment, as the process of the first aspect of the present invention, crystal 1-kestose in the form of columnar crystals having lengths of 0.3 mm or longer (preferably 0.3 to 2 mm, more preferably 0.5 to 1.2 mm) and a purity of 95% or higher.

Furthermore, as in the process of the first aspect of the present invention, crystal 1-kestose may be prepared in continuous processes by repeating the same procedure as described above or carrying out the procedure of the first aspect of the present invention on the sugar solution containing 1-kestose from which crystal 1-kestose has been recovered. Alternatively, the same procedure as described above or the procedure of the first aspect of the present invention may be repeated on the sugar solution containing 1-kestose from which crystal 1-kestose has been recovered after replenishing the solution with fresh crystallizing sample. These continuous procedures of crystallization would help further increase the yield of 1-kestose crystals.

Process of the Third Aspect of the Present Invention

According to the third aspect of the present invention, there is provided a process for producing 1-kestose from sucrose using an enzyme derived from a certain microorganism.

Regarding the third aspect of the present invention, 1 unit of enzyme having fructose transferase activity refers to the following meaning:

In the case of an enzyme derived from an Asperaillus microorganism, the quantity of enzyme which can produce 1 $\mu$mol of 1-kestose in 1 minute at 40° C., pH 5.0, and a substrate (sucrose) concentration of 10 wt %;

In the case of an enzyme derived from a Penicillium microorganism, the quantity of enzyme which can produce 1 $\mu$mol of 1-kestose in 1 minute at 50° C., pH 7.0, and a substrate (sucrose) concentration of 10 wt %; and In the case of an enzyme derived from a Scopulariopsis microorganism, the quantity of enzyme which can produce 1 $\mu$mol of 1-kestose in 1 minute at 40° C., pH 7.0, and a substrate (sucrose) concentration of 10 wt %.

Step (i): Synthesis of 1-Kestose from Sucrose

In the process according to the third aspect of the present invention, sucrose is first converted to 1-kestose in either of the following steps:

(i) (1) allowing an enzyme having fructose transferase activity derived from an Aspergillus microorganism to react on a sucrose solution to produce 1-kestose accounting for 43 wt % or more of the resultant sugars;

(2) allowing an enzyme having fructose transferase activity derived from a Penicillium microorganism to react on a sucrose solution to produce 1-kestose accounting for 46 wt % or more of the resultant sugars; or (3) allowing an enzyme having fructose transferase activity derived from a Scopulariopsis microorganism to react on a sucrose solution to produce 1-kestose accounting for 53 wt % or more of the resultant sugars.

Step (i)(1)

In step (i)(1), an enzyme having fructose transferase activity which can be prepared from an Asperaillus microorganism is used. The enzyme can be prepared preferably from *Aspergillus niger*, specifically from *Aspergillus niger* ATCC20611.

The enzyme can be recovered from a culture by incubating the microorganism in a suitable medium (e.g., a medium containing 3.0 to 10.0% of sucrose, 3.0 to 10.0% of yeast extract, and 0.3 to 1.0% of CMC) at initial pH of 6.0 to 7.0 and a temperature of 25 to 30° C. for 48 to 96 hours.

The enzyme acts on a sucrose solution with a concentration of 50 wt % or higher, preferably at a rate of 0.5 to 100 units per 1 g of sucrose, at pH 5.0 to 10.0 and a temperature of 50 to 65° C. and produces 1-kestose accounting for 43 wt % or more of the resultant sugars. Furthermore, it acts on a sucrose solution under the same conditions and produces nystose accounting for 13 wt % or less of the resultant sugars. In the processes described in Japanese Patent Publication No. 62184/1988 and Japanese Patent Laid-Open Publication No. 268190/1986, the rates of conversion from sucrose to 1-kestose are only 36 to 41% at maximum. In these processes, 11 to 23% of nystose is produced along with 1-kestose. The process according to the present invention has a marked advantage over the prior art described in the publications in selectively producing 1-kestose.

In the present invention, the enzyme is allowed to react on sucrose to produce 1-kestose. In a preferred embodiment of the present invention, a sucrose solution with a concentration of 50 wt % or higher, preferably 50 wt % to 60 wt %, is allowed to react at pH 5.0 to 10.0, preferably at pH 5.5 to 10.0, and a temperature of 50 to 65° C., preferably 50 to 60° C. Furthermore, in a preferred embodiment of the present invention, the enzyme having fructose transferase activity is allowed to react with sucrose solution at a rate of 0.5 to 100 units, preferably 3 to 100 units, per 1 g of sucrose and a temperature of 50 to 65° C., preferably 50 to 60° C., for 2 to 100 hours, preferably for 2 to 40 hours.

It is preferable that the enzyme be deactivated after the transfer reaction is over, preferably by adding activated carbon (e.g., Taiko activated carbon S-W50) at a rate of 0.1 to 1.0 wt % of the solids content and heating the reacting solution at a temperature of 90 to 95° C. for 20 minutes to 60 minutes, concurrently with the decoloration of the reacting solution.

In a preferred embodiment of the present invention, the resultant sugars contain 43 wt % or more of 1-kestose and 13 wt % or less of nystose. The composition can be improved under more preferable conditions to 44 wt % or more of 1-kestose and 7 wt % or less of nystose.

Step (i)(2)

The enzyme for use in step (i)(2) is an enzyme derived from a Penicillium species which can act on sucrose to produce 1-kestose accounting for 46 wt % or more of the resultant sugars. Enzymes having fructose transferase activity which are used preferably in the present invention include the novel enzyme described below:

The enzyme is prepared from a Penicillium microorganism, preferably from *Penicillium roqueforti*, specifically *Penicillium roqueforti* IAM7254 strain.

The enzyme can be recovered from a culture by incubating the microorganism in a suitable medium (e.g., a medium containing 5 to 30% of sucrose, 1 to 10% of corn steep liquor, 0.05 to 0.3% of urea, 0.2 to 3.0 of potassium dihydrogenphosphate, and 0.01 to 0.1% of magnesium sulfate heptahydrate), at initial pH of 6.5 to 7.5 and a temperature of 25 to 30° C. for 2 to 5 days.

It is preferable that the enzyme be purified by a known purification method. Preferable purification methods include salting out using a salt such as ammonium sulfate; precipitation using an organic solvent such as methanol; ethanol or acetone, adsorption using starch; ultrafiltration; gel filtration chromatography; ion exchange chromatography; and various other chromatographic procedures.

The novel enzyme showed the following properties:
Activity

The enzyme cuts the β-D-fructofuranoside bond of a sugar having a β-D-fructofuranoside bond, such as sucrose, 1-kestose or raffinose, and transfers the resultant fructosyl group specifically to the C-1 position (hydroxyl group) of the terminal fructosyl group of sugars.

The enzyme also acts on sucrose solution with a concentration of 50 wt % or higher at pH 6.0 to 9.0 and a temperature of 35 to 55° C. to produce 1-kestose accounting for 46 wt % or more of the resultant sugars.

The enzyme can react with a sucrose solution with a concentration of 50 wt % or higher at a rate of 0.5 to 100 units per 1 g of sucrose, at pH 6.0 to 9.0 and a temperature of 35 to 55° C. for 2 to 100 hours, to produce 1-kestose accounting for 46 wt % or more of the resultant sugars. The enzyme also acts on a sucrose solution under the same conditions to produce nystose accounting for 7 wt % or less of the resultant sugars. In this sense, the enzyme is significantly suitable in selectively producing 1-kestose.

Substrate Specificity

The enzyme effectively acts on sucrose, 1-kestose, raffinose, but not on turanose, maltose.

Optimum Temperature

The optimum temperature of the enzyme is 40 to 50° C.

Stability to Temperature

The enzyme retains at least 60% of relative activity at pH 7.0 and 55° C. or less after 30 minutes.

Optimum pH

The optimum pH of the enzyme is 6.0 to 7.0.

Stable pH

The enzyme is remarkably stable in the range of pH 4.0 to 8.0, retaining at least 90% of relative activity at 40° C. after 30 minutes.

Molecular Weight

The molecular weight of the enzyme as measured by gel filtration chromatography is 315,000.

Inhibition of Activity

The enzyme is inhibited by glucose, which is a byproduct of the fructose transfer reaction.

Enzyme Kinetics

The enzyme's km is 1.1 M.

In step (i)(2) of the present invention, the enzyme is allowed to react on sucrose to produce 1-kestose. According to a preferred embodiment of the present invention, a sucrose solution with a concentration 50 wt % or higher, preferably 55 to 65 wt %, is allowed to react at pH 6.0 to 9.0, preferably 6.0 to 8.0, and a temperature of 35 to 55° C., preferably 40 to 50° C. Further, according to a preferred embodiment of the present invention, the enzyme having fructose transferase activity is added to a sucrose solution at a rate of 0.5 to 100 units, preferably 2 to 50 units, per 1 g of sucrose to react at a temperature of 35 to 55° C., preferably 40 to 50° C., for 2 to 100 hours, preferably 4 to 100 hours.

It is preferable that the enzyme be deactivated after the transfer reaction is over, preferably by adding activated carbon (e.g., Taiko activated carbon S-W50) at a rate of 0.1 to 1.0 wt % of the solids content and heating the reacting solution at a temperature of 40 to 70° C. for 20 minutes to 60 minutes, concurrently with the decoloration of the reacting solution.

According to a preferred embodiment of the present invention, the resultant sugars contain 46 wt % or more of 1-kestose and 7 wt % or less of nystose.

Step (i)(3)

The enzyme for use in step (i)(3) is an enzyme derived from a Scopulariopsis species which can act on sucrose to produce 1-kestose accounting for 53 wt % or more of the resultant sugars. Enzymes having fructose transferase activity which are used preferably in the present invention include the novel enzyme described below:

The enzyme is prepared from a Scopulariopsis microorganism, preferably from *Scopulariopsis brevicaulis*, specifically *Scopulariopsis brevicaulis* IF04843 strain.

The enzyme can be recovered from a culture by incubating the microorganism in a suitable medium (e.g., a medium containing 3.0 to 10.0% of sucrose, 5 to 15% of corn steep liquor, 0.05 to 0.3% of urea, 0.2 to 3.0 of potassium dihydrogenphosphate, and 0.01 to 0.1% of magnesium sulfate heptahydrate), at initial pH of 6.5 to 7.5 and a temperature of 20 to 30° C. for 3 to 8 days. The enzyme is prepared preferably by recovering the fungus body from the culture using a centrifuge such as a basket type; suspending the recovered fungus body in a buffer at pH 7.0; obtaining a crude enzyme suspension by an ultrasonic treatment and a membrane treatment; then treating with anion exchange, gel filtration, chromatographic focusing, or other procedure on the crude enzyme suspension.

The novel enzyme showed the following properties:

Activity

The enzyme cuts the β-D-fructofuranoside bond of a sugar having a β-D-fructofuranoside bond, such as sucrose, 1-kestose or raffinose, and transfers the resultant fructosyl group specifically to the C-1 position (hydroxyl group) of the terminal fructosyl group of sugars.

The enzyme also acts on a sucrose solution with a concentration of 50 wt % or higher at pH 6.0 to 10.0 and a temperature of 35 to 50° C. to produce 1-kestose accounting for 53 wt % or more of the resultant sugars.

The enzyme can react with a sucrose solution with a concentration of 50 wt % or higher, preferably 50% to 55 wt % at pH 6.0 to 10.0, preferably 7.0 to 9.8, and a temperature of 35 to 50° C., preferably 35 to 40° C., to produce 1-kestose accounting for 53 wt % or more of the resultant sugars. Preferably, the enzyme is allowed to react at a rate of 0.5 to 100 units, more preferably 2 to 20 units, per 1 g of sucrose. The enzyme according to the present invention also acts on a sucrose solution under the same conditions to produce nystose accounting for 5 wt % or less of the resultant sugars. In this sense, the enzyme is significantly suitable in selectively producing 1-kestose.

Substrate Specificity

The enzyme effectively acts on sucrose, 1-kestose, raffinose, but not on turanose, maltose.

Optimum Temperature

The optimum temperature of the enzyme is 40° C.

Optimum pH

The optimum pH of the enzyme is 7.0.

Stable pH

The enzyme is remarkably stable in the range of pH 6.0 to 10.0, retaining at least 80% of relative activity at 40° C. after 30 minutes.

Molecular Weight

The molecular weight of the enzyme as measured by gel filtration chromatography is 360 to 380 kDa.

An analysis by SDS-PAGE has revealed that the enzyme has a molecular weight of about 54 kDa and comprises a subunit with a molecular weight of about 51 kDa with the glycoside chain removed.

Isoelectric Point

The isoelectric point as measured by two dimensional electrophoresis and hydrophobic chromatography is about 3.8 to 3.9.

Inhibition of Activity

The enzyme is inhibited by glucose, which is a byproduct of the fructose transfer reaction.

Enzyme Kinetics

The enzyme's km is 0.75 M. The enzyme is uncompetitively inhibited by glucose with an inhibition constant (Ki) of 0.125 M.

In step (i)(3) of the present invention, the enzyme is allowed to react on sucrose to produce 1-kestose. According to a preferred embodiment of the present invention, a sucrose solution with a concentration 50 wt % or higher, preferably 50 to 55 wt %, is allowed to react at pH 6.0 to 10.0, preferably 7.0 to 9.8, and a temperature of 35 to 50° C., preferably 35 to 40° C. Further, according to a preferred embodiment of the present invention, the enzyme having fructose transferase activity is added to a sucrose solution at a rate of 0.5 to 100 units, preferably 2 to 20 units, per 1 g of sucrose to react at a temperature of 35 to 50° C., preferably 35 to 40° C., for 2 to 100 hours, preferably 9 to 60 hours.

It is preferable that the enzyme be deactivated after the transfer reaction is over, preferably by adding activated carbon (e.g., Taiko activated carbon S-W50) at a rate of 0.1 to 1.0 wt % of the solids content and heating the reacting solution at a temperature of 90 to 95° C. for 20 minutes to 60 minutes, concurrently with the decoloration of the reacting solution.

According to a preferred embodiment of the present invention, the resultant sugars contain 53 wt % or more of 1-kestose and 5 wt % or less of nystose. The composition can be improved under more preferable conditions to 55 wt % or more of 1-kestose and 4 wt % or less of nystose.

According to a preferred embodiment of the present invention, it is desired that the solution containing 1-kestose which has been obtained in either of steps (i)(1) through (3) above be filtered to remove fungus body, etc., and decolorized and deodorized by using activated carbon, prior to the subsequent step (ii). Decoloration and deodorization may be achieved by adding activated carbon accounting for about 0.1 to 1.0 wt % of the solids content in the 1-kestose solution and stirring at a temperature of 40 to 70° C. for 20 to 60 minutes. It is preferable that the solution be further desalted with cation and anion exchange resin to desalt and filtered again to provide a colorless and transparent 1-kestose solution.

Step (ii): Chromatographic Separation

The reacting solution containing 1-kestose, which has been obtained using the above enzyme, is chromatographically separated to prepare crystal 1-kestose. A preferred method of chromatographic separation is simulated-moving bed chromatographic separation, which is generally used for producing isomerized sugars.

The chromatographic separation provides a fraction containing 1-kestose at a purity of 80% or higher, preferably 90% or higher.

In the process according to the present invention, the relative content of sugars of which molecular weights are higher than that of 1-kestose, such as nystose, is low as already explained. Therefore, 1-kestose can effectively be purified by a single procedure of two-component simulated-moving bed chromatographic separation using the enzyme and reacting conditions as described in step (i), Crn. while two or more repeated operations are required in the prior art. A preferred embodiment of the present invention enables 1-kestose to be purified to 80 to 95% by the this procedure.

In this step, a fraction containing 1-kestose at a purity of 80%, preferably 90% or higher, is obtained. It is preferable that the highly pure 1-kestose solution be separated to minimize the proportion of nystose in the remaining sugar content, as a lower nystose content would result in larger crystals of 1-kestose. It is desired that the nystose content be 10 wt % or less of 1-kestose.

According to a preferred embodiment of the present invention, it is preferable that the obtained fraction be treated with activated carbon and desalted before proceeding to the subsequent step (iii). Treating with activated carbon and desalting may be performed in the same manner as in step (i).

Step (iii): Crystallization

In the third aspect of the present invention, step (iii) is a crystallizing step. The procedure for step (iii) may preferably be the same as in the first or second aspect of the present invention. Similarly, the preferred embodiment of the first and second aspects of the present invention may also be applicable as the preferred embodiment of the third aspect of the present invention.

Crystal 1-Kestose

According to the preferred embodiments of the present invention, granular crystal 1-kestose having grain sizes of 0.3 to 2 mm, preferably 0.5 to 1.2 mm can be obtained. Unlike powdery crystals, large crystals of 1-kestose do not easily coagulate while drying, making it possible to obtain a product of a uniform grain size. Furthermore, the crystal 1-kestose according to the present invention has high fluidity and, therefore, is less likely to dust or consolidate. Advantages expected from this characteristic include little deviation in small packages such as for table sugar, and little classification when mixed with granulated sugar.

EXAMPLES

The present invention is further illustrated by the following examples which are not intended as a limitation of the invention. Figures in percentage hereafter refer to wt % unless otherwise specified.

In the following examples, the crystallizing sample used was prepared by procedures such as chromatographically separating and purifying from a commercially available mixture of fructooligosaccharides, Meioligo G or Meioligo P (Meiji Seika), or chromatographically separating and purifying from a sucrose solution which had been allowed to react with fructose transferase as described in the following examples.

In the following examples, the sugar composition in the crystallizing sample varies, reflecting the difference in the separating conditions.

Example A

Example A1

A crystallizing sample with a sugar composition of 92% of 1-kestose, 5% of sucrose, and 3% of nystose, which had been prepared according to Example C1 as described later, was used.

The crystallizing sample was concentrated to a Brix of 80. Then, after heating the concentrate to a temperature of 75° C., seed crystals of 1-kestose accounting for 1% of the solids content in the concentrate were added. Crystals were allowed to grow for 0.5 hour. The solution was then concentrated under a reduced pressure at an absolute pressure of 80 mmHg for 30 minutes. Through the concentration procedure, the temperature of the solution dropped to 55° C., and the Brix became 83. As microcrystals of 1-kestose were generated during the concentration procedure, the concentrate was heated at 75° C. and maintained at the temperature for 1 hour to dissolve the microcrystals. As a result, the Brix of the portion of the concentrate except the crystals became approximately 80.

The crystal growing step and the microcrystal dissolving step above were repeated four times to allow 1-kestose to crystallize sufficiently. Then, the crystals were recovered by centrifugation at room temperature, and dried to finally make 1-kestose crystals.

The purity of the 1-kestose crystals obtained was 99%, and the yield of crystals was approximately 60%.

A microscopic examination revealed that the majority of the crystals ranged from 0.3 to 2 mm in length, and that there was no crystal coagulation.

The grain size distribution of the crystals was investigated by screening the crystals through 20, 40 and 60 mesh automatic sieves for 5 minutes. The result is shown in the table below. The prevailing crystal size was found to be 0.5 mm to 1.2 mm in length. It should be noted that the actual lengths of the oversize crystals exceeded the diagonal length of the mesh, considering that the crystals of 1-kestose have rectangular shapes.

TABLE 1

| Mesh | Side length | Diagonal length | oversize |
|------|-------------|-----------------|----------|
| 20   | 0.84        | 1.19            | 0.5%     |
|      |             |                 | 75.9%    |
| 40   | 0.37        | 0.52            | 18.1%    |
| 60   | 0.25        | 0.35            | 5.5%     |

Example A2

A crystallizing sample with a sugar composition of 95% of 1-kestose, 4% of sucrose, and 1% of nystose, which had been prepared according to Example D2 as described later, was used.

The crystallizing sample was concentrated to a Brix of 80. Then, after heating the concentrate to a temperature of 80° C., seed crystals of 1-kestose accounting for 0.5% of the solids content in the concentrate were added. Crystals were allowed to grow for 0.5 hour. The solution was then concentrated under a reduced pressure at an absolute pressure of 160 mmHg for 30 minutes. Through the concentration procedure, the temperature of the solution dropped to 70° C., and the Brix became 83. As microcrystals of 1-kestose were generated during the concentration procedure, the concentrate was heated at 95° C. and maintained at the temperature for 1 hour to dissolve the microcrystals.

The crystal growing step and the microcrystal dissolving step above were repeated four times. As microcrystals failed to dissolve completely in the fourth microcrystal dissolving step, water accounting for about 2% of the solids content in the concentrate was added to dissolve the microcrystals. Then, the crystal growing step and the microcrystal dissolving step above were repeated two more times. Then, the crystals were recovered by centrifugation at room temperature, and dried to finally make 1-kestose crystals.

The purity of the 1-kestose crystals obtained was 99%, and the yield of crystals was approximately 57%. A microscopic examination revealed that the a majority of the crystals were about 1 mm in length.

Example A3

A crystallizing sample with a sugar composition of 95% of 1-kestose, 4% of sucrose, and 1% of nystose, which had been prepared according to Example D2 as described later, was used.

The crystallizing sample was concentrated to a Brix of 75. Then, after heating the concentrate to a temperature of 70°

C., the solution was concentrated at an absolute pressure of 80 mmHg for 15 minutes to produce microcrystals. With the microcrystals as nuclei, crystals were allowed to grow at 70° C. for 6.0 hours. The solution was then concentrated under a reduced pressure at an absolute pressure of 80 mmHg for 30 minutes. Through the concentration procedure, the temperature of the solution dropped to 55° C. As microcrystals of 1-kestose were generated during the concentration procedure, the concentrate was heated at 75° C. and maintained at the temperature for 1 hour to dissolve the microcrystals.

The crystal growing step and the microcrystal dissolving step above were repeated four times to allow 1-kestose to crystallize sufficiently. Then, the crystals were recovered by centrifugation at room temperature, and dried to finally make 1-kestose crystals.

The purity of the 1-kestose crystals obtained was 99%, and the yield of crystals was approximately 59%. A microscopic examination revealed that the a majority of the crystals were about 1 mm in length.

The grain size distribution of the crystals was investigated by screening the crystals through 20, 24, 32 and 42 mesh sieves.

The result is shown in the table below. The prevailing crystal size was found to be 0.7 mm to 1.2 mm in length. It should be noted that the actual lengths of the oversize crystals exceeded the diagonal length of the mesh, considering that the crystals of 1-kestose have rectangular shapes.

TABLE 2

| Mesh | Side length | Diagonal length | oversize |
| --- | --- | --- | --- |
| 20 | 0.84 | 1.19 | 6.5% |
|  |  |  | 35.8% |
| 24 | 0.71 | 1.00 | 41.7% |
| 32 | 0.50 | 0.70 | 13.8% |
| 42 | 0.35 | 0.49 | 2.2% |

Example A4

A crystallizing sample with a sugar composition of 92% of 1-kestose, 2% of sucrose, and 6% of nystose was prepared from Meioligo P by chromatographic separation using a two-component simulated-moving bed chromatographic separator.

The crystallizing sample was concentrated to a Brix of 80. Then, after heating the concentrate to a temperature of 70° C., the solution was concentrated at an absolute pressure of 80 mmHg for 10 minutes to produce microcrystals. With the microcrystals as nuclei, crystals were allowed to grow at 70° C. for 3 hours. The solution was then concentrated under a reduced pressure at an absolute pressure of 80 mmHg for 30 minutes. Through the concentration procedure, the temperature of the solution cooled to 55° C. As microcrystals of 1-kestose were generated during the concentration procedure, the concentrate was heated at 75° C. and maintained at the temperature for 1 hour to dissolve the microcrystals.

The crystal growing step and the microcrystal dissolving step above were repeated three times. The crystallizing sample was added to make up for the loss in volume caused in the concentration procedure. Then, the crystal growing step and the microcrystal dissolving step above were repeated two more times. Then, the crystals were recovered by centrifugation at room temperature, and dried to finally make 1-kestose crystals.

The purity of the 1-kestose crystals obtained was 99%, and the yield of crystals was approximately 60%. A microscopic examination revealed that the a majority of the crystals ranged approximately from 0.3 to 1 mm in length.

Example A5

A crystallizing sample with a sugar composition of 95% of 1-kestose, 4% of sucrose, and 1% of nystose, which had been prepared according to Example D2 as described later, was used.

The crystallizing sample was concentrated to a Brix of 85. Then, after heating the concentrate to a temperature of 80° C., seed crystals of 1-kestose accounting for 0.5% of the solids content in the concentrate were added. Crystals were allowed to grow for 30 minutes. After the solution was cooled to 70° C., taking 30 minutes, crystals were allowed to grow at 70° C. for 30 minutes. Further, after the solution was cooled to 60° C., taking 40 minutes, crystals were allowed to grow at 60° C. for 30 minutes. Furthermore, after the solution was cooled to 50° C., taking 60 minutes, crystals were allowed to grow at 50° C. for 30 minutes.

Then, the crystals were recovered by centrifugation at room temperature, and dried to finally make 1-kestose crystals.

The purity of the 1-kestose crystals obtained was 98%, and the yield of crystals was approximately 45%. A microscopic examination revealed that the a majority of the crystals ranged approximately from 0.3 to 2 mm in length.

Example A6

A crystallizing sample with a sugar composition of 95% of 1-kestose, 4% of sucrose, and 1% of nystose, which had been prepared according to Example D2 as described later, was used.

The crystallizing sample was concentrated to a Brix of 85. Then, the concentrate was heated gradually from 20° C. to 80° C. to produce microcrystals at around 50 to 60° C. With the microcrystals as nuclei, crystals were allowed to grow at 80° C. for 30 minutes. After the solution was cooled to 70° C., taking 30 minutes, crystals were allowed to grow at 70° C. for 30 minutes. Further, after the solution was cooled to 60° C., taking 40 minutes, crystals were allowed to grow at 60° C. for 30 minutes. Furthermore, after the solution was cooled to 50° C., taking 60 minutes, crystals were allowed to grow at 50° C. for 30 minutes.

Then, the crystals were recovered by centrifugation at room temperature, and dried to finally make 1-kestose crystals.

The purity of the 1-kestose crystals obtained was 99%, and the yield of crystals was approximately 43%. A microscopic examination revealed that the majority of the crystals ranged approximately from 0.3 to 2 mm in length.

Example A7

A crystallizing sample with a sugar composition of 95% of 1-kestose, 4% of sucrose, and 1% of nystose, which had been prepared according to Example D2 as described later, was used.

The crystallizing sample was crystallized in a continuous crystallization procedure.

The crystallizing sample was concentrated to a Brix of 85. Seed crystals of 1-kestose accounting for 0.1% of the solids content in the concentrate were added. Crystals were allowed to grow at 80° C. for 30 minutes. After the solution was cooled to 70° C., taking 30 minutes, crystals were allowed to grow at 70° C. for 30 minutes. Further, after the solution was cooled to 60° C., taking 40 minutes, crystals were allowed to grow at 60° C. for 30 minutes. Furthermore, after the solution was cooled to 50° C., taking 60 minutes, crystals were allowed to grow at 50° C. for 30 minutes. Finally, after the solution was cooled to 30° C., taking 120 minutes, crystals were allowed to grow at 30° C. for 6 hours. The crystals were recovered by centrifugation at room temperature, and dried to finally make 1-kestose crystals.

The purity of the 1-kestose crystals obtained was 99%, and the yield of crystals was approximately 51%.

As the purity of 1-kestose in the molasses was 92%, it was concentrated to a Brix of 84, and crystallized in the same procedure. The purity of the 1-kestose crystals obtained was 97%, and the yield of crystals was approximately 44%.

The total yield of 1-kestose so far was 72%.

Then, as the purity of 1-kestose in the molasses was 89%, it was concentrated to a Brix of 84, and crystallized in the same procedure. The purity of the 1-kestose crystals obtained was 95%, and the yield of crystals was approximately 55%. The total yield of 1-kestose so far was 85%.

As the purity of 1-kestose in the molasses was 79%, it was concentrated to a Brix of 84, and crystallized in the same procedure. However, separation at room temperature was impracticable due to extensive deposition of microcrystals.

Example A8

A crystallizing sample with a sugar composition of 95% of 1-kestose, 4% of sucrose, and 1% of nystose, which had been prepared according to Example D2 as described later, was used.

The crystallizing sample was concentrated to a Brix of 85. Then, after heating the concentrate to a temperature of 80° C., seed crystals of 1-kestose accounting for 0.5% of the solids content in the concentrate were added. Crystals were allowed to grow at 80° C. for 15 hours. After the solution was cooled to 60° C., taking 2 hours, crystals were allowed to grow at 60° C. for 5 hours. Furthermore, after the solution was cooled to 40° C., taking 4 hours, crystals were allowed to grow at 40° C. for 48 hours. The crystals were recovered by centrifugation at room temperature, and dried to finally make 1-kestose crystals.

The purity of the 1-kestose crystals obtained was 99%, and the yield of crystals was approximately 50%. A microscopic examination revealed that the majority of the crystals ranged approximately from 0.3 to 2 mm in length.

The grain size distribution of the crystals was investigated by screening the crystals through 20, 24, 32 and 42 mesh sieves.

The result is shown in the table below. The prevailing crystal size was found to be 1.0 mm to 1.2 mm in length. It should be noted that the actual lengths of the oversize crystals exceeded the diagonal length of the mesh, considering that the crystals of 1-kestose have rectangular shapes.

TABLE 3

| Mesh | Side length | Diagonal length | oversize |
| --- | --- | --- | --- |
| 20 | 0.84 | 1.19 | 7.3% |
|  |  |  | 68.5% |
| 24 | 0.71 | 1.00 | 16.0% |

TABLE 3-continued

| Mesh | Side length | Diagonal length | oversize |
| --- | --- | --- | --- |
| 32 | 0.50 | 0.70 | 6.4% |
| 42 | 0.35 | 0.49 | 1.8% |

Comparative Example

The crystal 1-kestose prepared in Example A above was mixed with sucrose and examined for the properties of the mixture.

The crystal 1-kestose prepared in Example A2 and granulated sugar HA (Nippon Beet Sugar) were screened separately. The 40 mesh oversize portion of each was mixed together at a rate of 80% of sucrose and 20% of 1-kestose and used as a coarse (40 mesh oversize) mixture sample of sucrose and 1-kestose.

In addition, crystal 1-kestose prepared in Example A2 above and granulated sugar HA (Nippon Beet Sugar) were separately crushed with a table grinder and screened. The 100 mesh undersize portion of each was mixed together at a rate of 80% of sucrose and 20% of 1-kestose and used as a fine mixture sample of sucrose and 1-kestose.

These samples were analyzed using a powder tester (Hosokawa Micron) for the items listed in the table below according to standard procedures. The results are shown in the table below:

TABLE 4

| Item | Fine sample | Coarse sample |
| --- | --- | --- |
| Fluidity |  |  |
| Angle of repose | 49 | 39 |
| Spatula angle | 65 | 40 |
| Compressibility | 49 | 13 |
| Dispersibility | 27 | 11 |
| Variation as packed | Poor | Good |

These results show that the coarse sample had superior fluidity and less variation as packed. The fine sample was found to consolidate when compressed.

Example B

Example B1

(1) A 15 L of medium containing 5% of sucrose, 6.5% of yeast extract, and 0.5% of CMC(caroboxymetyl cellulose) was placed in a 30 L jar fermenter, adjusted to pH 6.5, and sterilized at 120° C. for 30 minutes. *Asperaillus niger* ATCC20611 was inoculated in a medium placed in a 1 L Erlenmeyer flask and containing 5.0% of sucrose, 2.0% of powdered bouillon, and 0.5% of CMC and incubated at 28° C. for 21 hours, then implanted in the above medium and incubated at 28° C. for 96 hours. After incubation was over, fungus body was recovered from the culture, using a basket type centrifuge, and freeze-dried to make dried fungus body for use as enzyme in the following reactions.

The fructose transferase activity of the dried fungus body was approximately 14,000 units per 1 g of dried fungus body.

(2) 10 L of sucrose solution adjusted to a concentration of 60%, pH 10.0, and a temperature of 60° C. was placed in a reaction chamber. The enzyme which had been prepared in (1) above was added to the reaction chamber at a rate of 60 units per 1 g of sucrose, and allowed to react at a temperature of 60° C. and pH 10.0 for 40 hours. Then, activated carbon (Taiko activated carbon S-W50) was added at a rate of 1.0% of the solids content to deactivate the enzyme and decolorize the solution at a temperature of 95° C. for 30 minutes.

The sugar composition of the deactivated solution was 44% of 1-kestose, 32% of sucrose, 17% of monosaccharides, and 7% of nystose.

The deactivated solution was filtered to remove any impurities such as the fungus body and the activated carbon. Then, activated carbon (Taiko activated carbon S-W50) was added to the filtrate at a rate of 0.5% of the solids content, and stirred at a temperature of 60° C. for 20 minutes to decolorize again. After filtrating to remove the activated carbon in the same manner as above, the solution was desalted through cation and anion exchange resin, then filtrated again to make a colorless and transparent 1-kestose solution (chromatographic sample). In the decolorizing and desalting procedure, the decomposition of 1-kestose was hardly observed.

In order to improve the purity of 1-kestose in the chromatographic sample obtained above, the solution was chromatographically separated by a two-component simulated-moving bed chromatographic separator. A chromatographic fraction with a sugar composition of 92% of 1-kestose, 3% of sucrose, and 5% of nystose was obtained.

Then, the chromatographic fraction was decolorized and desalted to make a colorless and transparent 1-kestose fraction (crystallizing sample).

Example B2

Enzyme which had been prepared in the same manner as in Example B1 (1) was added to 10 L of sucrose solution adjusted to a concentration of 50%, pH 9.0, and a temperature of 50° C. at a rate of 100 units per 1 g of sucrose, and allowed to react at a temperature of 50° C. and pH 9.0 for 2 hours. Then, activated carbon (Taiko activated carbon S-W50) was added at a rate of 1.0% of the solids content to deactivate the enzyme and decolorize the solution at a temperature of 95° C. for 30 minutes.

The sugar composition of the deactivated solution was 43% of 1-kestose, 30% of sucrose, 18% of monosaccharides, and 9% of nystose.

The deactivated solution was filtered to remove any impurities such as the fungus body and the activated carbon. Then, activated carbon (Taiko activated carbon S-W50) was added to the filtrate at a rate of 0.5% per solids content, and stirred at a temperature of 60° C. for 20 minutes to decolorize again. After filtrating to remove the activated carbon in the same manner as above, the solution was desalted through cation and anion exchange resin, then filtrated again to make a colorless and transparent 1-kestose solution (chromatographic sample). In the decolorizing and desalting procedure, the decomposition of 1-kestose was hardly observed.

In order to improve the purity of 1-kestose in the chromatographic sample obtained above, the solution was chromatographically separated by a two-component simulated-moving bed chromatographic separator. A chromatographic fraction with a sugar composition of 90% of 1-kestose, 3% of sucrose, and 7% of nystose was obtained.

Then, the chromatographic fraction was decolorized and desalted to make a colorless and transparent 1-kestose fraction (crystallizing sample).

Example B3

Enzyme which had been prepared in the same manner as in Example B1 (1) was added to 10 L of sucrose solution adjusted to a concentration of 60%, pH 5.5, and a temperature of 60° C. at a rate of 3.0 units per 1 g of sucrose, and allowed to react at a temperature of 60° C. and pH 5.5 for 4 hours. Then, activated carbon (Taiko activated carbon S-W50) was added at a rate of 0.3% of the solids content to deactivate the enzyme and decolorize the solution at a temperature of 95° C. for 30 minutes.

The sugar composition of the deactivated solution was 43% of 1-kestose, 22% of sucrose, 22% of monosaccharides, and 13% of nystose.

The deactivated solution was filtered to remove any impurities such as the fungus body and the activated carbon. Then, activated carbon (Taiko activated carbon S-W50) was added to the filtrate at a rate of 0.2% per solids content, and stirred at a temperature of 60° C. for 20 minutes to decolorize again. After filtrating to remove the activated carbon in the same manner as above, the solution was desalted through cation and anion exchange resin, then filtrated again to make a colorless and transparent 1-kestose solution (chromatographic sample). In the decolorizing and desalting procedure, the decomposition of 1-kestose was hardly observed.

In order to improve the purity of 1-kestose in the 1-kestose solution obtained above, the solution was chromatographically separated by a two-component simulated-moving bed chromatographic separator. A chromatographic fraction with a sugar composition of 80% of 1-kestose, 7% of sucrose, and 13% of nystose was obtained.

Then, the chromatographic fraction was decolorized and desalted to make a colorless and transparent 1-kestose fraction (crystallizing sample).

Example B4

The crystallizing sample with a sugar composition of 90% of 1-kestose, 3% of sucrose, and 7% of nystose, which had been prepared according to the procedure as described in Example B2, was concentrated to a Brix of 80. After heating the concentrate to a temperature of 70° C., the solution was concentrated at an absolute pressure of 80 mmHg for 10 minutes to produce microcrystals. With the microcrystals as nuclei, crystals were allowed to grow at 70° C. for 3 hours. The solution was concentrated under a reduced pressure at an absolute pressure of 80 mmHg for 30 minutes. Through the concentration procedure, the temperature of the solution dropped to 55° C. As microcrystals of 1-kestose were generated during the concentration procedure, the concentrate was heated at 75° C. and maintained at the temperature for 1 hour to dissolve the microcrystals.

The crystal growing step and the microcrystal dissolving step above were repeated three times. The crystallizing sample was added to make up for the loss in volume caused in the concentration procedure. Then, the crystal growing step and the microcrystal dissolving step above were repeated two more times. Then, the crystals were recovered by centrifugation at room temperature, and dried to finally make 1-kestose crystals.

The purity of the 1-kestose crystals obtained was 99%, and the yield of crystals was approximately 60%.

A microscopic examination revealed that the majority of the crystals ranged approximately from 0.3 to 1 mm in length.

Example B5

A crystallizing sample with a sugar composition of 92% of 1-kestose, 3% of sucrose, and 5% of nystose, which had been prepared in Example B1, was crystallized in a continuous crystallization procedure.

The crystallizing sample was concentrated to a Brix of 85. Seed crystals of 1-kestose accounting for 0.1% of the solids content in the concentrate were added. Crystals were allowed to grow at 80° C. for 30 minutes. After the solution was cooled to 70° C., taking 30 minutes, crystals were allowed to grow at 70° C. for 30 minutes. Further, after the solution was cooled to 60° C., taking 40 minutes, crystals were allowed to grow at 60° C. for 30 minutes. Furthermore, after the solution was cooled to 50° C., taking 60 minutes, crystals were allowed to grow at 50° C. for 30 minutes. Finally, after the solution was cooled to 30° C., taking 120 minutes, crystals were allowed to grow at 30° C. for 6 hours. The crystals were recovered by centrifugation at room temperature, and dried to finally make 1-kestose crystals.

The purity of the 1-kestose crystals obtained was 99%, and the yield of crystals was approximately 51%.

As the purity of 1-kestose in the molasses was 85%, it was concentrated to a Brix of 84, and crystallized in the same procedure as above. The purity of the 1-kestose crystals obtained was 95%, and the yield of crystals was approximately 55%.

The total yield of 1-kestose so far was 78%.

Then, as the purity of 1-kestose in the molasses was 74%, it was concentrated to a Brix of 84, and crystallized in the same procedure as above. However, separation at room temperature was impracticable due to extensive deposition of microcrystals.

Example C

Example C1

(1) A 15 L of medium containing 22.5% of sucrose, 1.5% of yeast extract, and 3.0% of corn steep liquor was placed in a 30 L jar fermenter, adjusted to pH 6.8, and sterilized at 120° C. for 30 minutes. *Penicillium roqueforti* (IAM7254 strain) was inoculated in a medium placed in a 1 L Erlenmeyer flask and containing 15.0% of sucrose, 1.0% of yeast extract, and 2.0% of corn steep liquor and incubated at 28° C. for three days, then implanted in the above medium and incubated at 28° C. for four days. After incubation was over, fungus body was recovered from the culture, using a basket type centrifuge, and freeze-dried to make dried fungus body for use as enzyme in the following reactions.

The fructose transferase activity of the dried fungus body was approximately 95 to 135 units per 1 g of dried fungus body.

(2) Enzyme which had been prepared as described above was added to 10 L of sucrose solution adjusted to a concentration of 55 wt %, pH 7.0, and a temperature of 50° C., at a rate of 10 units per 1 g of sucrose, and allowed to react at a temperature of 50° C. and pH 7.0 for 4 hours. Then, activated carbon (Taiko activated carbon S-W50) was added at a rate of 0.3% of the solids content to deactivate the enzyme and decolorize the solution at a temperature of 95° C. for 30 minutes. The sugar composition of the solution was 46% of 1-kestose, 18% of sucrose, 30% of monosaccharides, and 6% of nystose. The deactivated solution was filtered to remove any impurities such as the fungus body. Then, the filtrate was decolorized and desalted through activated carbon and ion exchange resin, then filtrated again to make a colorless and transparent 1-kestose solution.

In order to improve the purity of 1-kestose in the 1-kestose solution obtained above, the solution was chromatographically separated by a two-component simulated-moving bed chromatographic separator. A chromatographic fraction with a sugar composition of 92% of 1-kestose, 5% of sucrose, and 3% of nystose was obtained.

Then, the chromatographic fraction was decolorized and desalted to make a colorless and transparent 1-kestose fraction (crystallizing sample).

Example C2

Enzyme which had been prepared as described in Example C1 (1) was added to 10 L of sucrose solution adjusted to a concentration of 65 wt %, pH 8.0, and a temperature of 40° C., at a rate of 50 units per 1 g of sucrose, and allowed to react at a temperature of 40° C. and pH 8.0 for 5 hours. Then, activated carbon (Taiko activated carbon S-W50) was added at a rate of 1.0% of the solids content to deactivate the enzyme and decolorize the solution at a temperature of 95° C. for 30 minutes.

The sugar composition of the solution was 47% of 1-kestose, 18% of sucrose, 28% of monosaccharides, and 7% of nystose.

The deactivated solution was filtered to remove any impurities such as the fungus body. Then, the filtrate was decolorized and desalted through activated carbon and ion exchange resin, then filtrated again to make a colorless and transparent 1-kestose solution (chromatographic sample).

In order to improve the purity of 1-kestose in the 1-kestose solution obtained above, the solution was chromatographically separated by a two-component simulated-moving bed chromatographic separator. A chromatographic fraction with a sugar composition of 90% of 1-kestose, 3% of sucrose, and 7% of nystose was obtained.

Then, the chromatographic fraction was decolorized and desalted to make a colorless and transparent 1-kestose fraction (crystallizing sample). The crystallizing sample thus prepared was treated in the same procedure as in Example B4 described above to finally make similar crystal 1-kestose.

Example C3

Enzyme which had been prepared as described in Example C1 (1) was added to 10 L of sucrose solution adjusted to a concentration of 65 wt %, pH 6.0, and a temperature of 40° C., at a rate of 2 units per 1 g of sucrose, and allowed to react at a temperature of 40° C. and pH 6.0 for 100 hours. Then, activated carbon (Taiko activated carbon S-W50) was added at a rate of 1.0% of the solids content to deactivate the enzyme and decolorize the solution at a temperature of 95° C. for 30 minutes.

The sugar composition of the solution was 46% of 1-kestose, 19% of sucrose, 28% of monosaccharides, and 7% of nystose.

The deactivated solution was filtered to remove any impurities such as the fungus body. Then, the filtrate was decolorized and desalted through activated carbon and ion exchange resin, then filtrated again to make a colorless and transparent 1-kestose solution (chromatographic sample).

In order to improve the purity of 1-kestose in the 1-kestose solution obtained above, the solution was chromatographically separated by a two-component simulated-moving bed chromatographic separator. A chromatographic fraction with a sugar composition of 80% of 1-kestose, 7% of sucrose, and 13% of nystose was obtained.

Then, the chromatographic fraction was decolorized and desalted to make a colorless and transparent 1-kestose fraction (crystallizing sample).

Example D

Example D1

(1) Purification of Enzyme

A 15 L of medium containing 5.0% of sucrose, 10.5% of corn steep liquor, and 0.1% of urea was placed in a 30L jar fermenter, adjusted to pH 7.0, and sterilized at 120° C. for 30 minutes. *Scopulariopsis brevicaulis* IFO4843 strain was inoculated in a medium placed in a 1 L Erlenmeyer flask and containing 5.0% of sucrose, 1.0% of yeast extract, and 2.0% of corn steep liquor and incubated at 28° C. for 29 hours, then implanted as fungus seeds and incubated at 28° C. for seven days. After incubation was over, fungus body was recovered from the culture, using a basket type centrifuge, and freeze-dried to make dried fungus body.

The fructose transferase activity of the dried fungus body was approximately 5.2 to 8.3 units per 1 g of dried fungus body.

The freeze-dried fungus body powder prepared above was suspended in a McIlvaine buffer (pH 7.0), and ultrasonically crushed. The crushed cells were ultrafiltrated through a membrane filter (cutoff molecular weight: 100,000). The supernatant obtained as crude enzyme was separated through an ion exchange column (Q-Sepharose column 60/100, Pharmacia), which had been equilibrated with Tris-HCl buffer (pH 7.3), at an NaCl gradient of 0 to 1 M. Two fractions which exhibited enzymatic activity were further purified through gel filtration chromatography (Superdex 200 10/30, Pharmacia). A resultant fraction which showed an electrophoretically single band (semi-purified enzyme) was then purified again by column chromatographic focusing (Mono P 5/20 column, Pharmacia), using 0.025 M bis-Tris-HCl (pH 6.3) as starting buffer, and polybuffer 74-HCl (pH 3.8) diluted 10 times as eluate.

The major conditions for the purification of the enzyme were as follows:

TABLE 5

|  | Solution (ml) | Total Enzyme Activity (Unit) | Yield (%) |
| --- | --- | --- | --- |
| Freeze-dried extent | 7700 | 219,000 | 100 |
| Ultrafilitration | 1200 | 228,600 | 104 |
| Anion exchange chromatography | 130 | 214,200 | 98 |
| Gel filtration chromatography | 15 | 657 | 0.3 |
| chromatographic focusing | 8 | 325 | 0.15 |

(2) Molecular Weight and Isoelectric Point

The molecular weight of the holoenzyme as found by gel filtration was approximately 360 to 380 kDa.

The result of SDS-PAGE suggested the existence of a subunit with a molecular weight of approximately 54 kDa.

The glycoside chain was removed by a method adapted from Muramatsu, et al. (Methods in Enzymology, 50, 555 (1987)) as follows: First, 1.2 times (w/w) of SDS per 1 μg enzyme was added to denature the enzyme in hot water bath; Then, with 1 milliunit of Endoglycosidase-β-H per 1 μg denatured protein added, the protein was incubated in 50 mM phosphate buffer (pH 6.0) at 37° C. for at least 12 hours; The result proved the existence of a subunit whose molecular weight was approximately 51 kDa with the glycoside chain removed.

The results of two-dimensional electrophoresis and hydrophobic chromatography showed that the estimated isoelectric point of the enzyme was 3.8 to 3.9.

Example D2

Enzyme which had been prepared as described in Example D1 was added to 10 L of sucrose solution adjusted to a concentration of 55 wt %, pH 9.8, and a temperature of 40° C., at a rate of 20 units per 1 g of sucrose, and allowed to react at a temperature of 40° C. and pH 9.8 for 9 hours. Then, activated carbon (Taiko activated carbon S-W50) was added at a rate of 1.0% of the solids content to deactivate the enzyme and decolorize the solution at a temperature of 95° C. for 30 minutes.

The sugar composition of the solution was 55% of 1-kestose, 16% of sucrose, 25% of monosaccharides, and 4% of nystose.

The deactivated solution was filtered to remove any impurities such as the activated carbon. Then, the filtrate was decolorized and desalted through activated carbon and ion exchange resin, then filtrated again to make a colorless and transparent 1-kestose solution.

In order to improve the purity of 1-kestose in the 1-kestose solution obtained above, the solution was chromatographically separated by a two-component simulated-moving bed chromatographic separator. A chromatographic fraction with a sugar composition of 95% of 1-kestose, 4% of sucrose, and 1% of nystose was obtained.

Then, the chromatographic fraction was decolorized and desalted to make a colorless and transparent 1-kestose fraction (crystallizing sample).

Example D3

Enzyme which had been prepared as described in Example D1 was added to 10 L of sucrose solution adjusted to a concentration of 50 wt %, pH 7.0, and a temperature of 35° C., at a rate of 2 units per 1 g of sucrose, and allowed to react at a temperature of 35° C. and pH 7.0 for 60 hours. Then, activated carbon (Taiko activated carbon S-W50) was added at a rate of 0.3% of the solids content to deactivate the enzyme and decolorize the solution at a temperature of 95° C. for 30 minutes.

The sugar composition of the solution was 53% of 1-kestose, 17% of sucrose, 25% of monosaccharides, and 5% of nystose.

The deactivated solution was filtered to remove any impurities such as the activated carbon. Then, the filtrate was decolorized and desalted through activated carbon and ion exchange resin, then filtrated again to make a colorless and transparent 1-kestose solution.

In order to improve the purity of 1-kestose in the 1-kestose solution obtained above, the solution was chromatographically separated by a two-component simulated-moving bed chromatographic separator. A chromatographic fraction with a sugar composition of 90% of 1-kestose, 3% of sucrose, and 7% of nystose was obtained.

Then, the chromatographic fraction was decolorized and desalted to make a colorless and transparent 1-kestose fraction (crystallizing sample). The crystallizing sample thus prepared was treated in the same procedure as in Example B4 described above, to finally make similar crystal 1-kestose.

What is claimed is:

1. A process for producing crystal 1-kestose comprising the steps of:

(a) concentrating a highly pure 1-kestose solution having 80% or more of 1-kestose to a Brix of at least 75, adding seed crystals, and then heating the resultant concentrate to a temperature of at least 60° C. to allow the crystals to grow, (b) concentrating the concentrate under a reduced pressure to allow the crystals to grow, (c) heating the concentrate to redissolve microcrystals which have been generated in the concentrate and, if the microcrystals fail to redissolve completely, adding water to the concentrate to dissolve the microcrystals, and (d) repeating at least once steps (b) and (c) and recovering the crystal 1-kestose.

2. A process for producing crystal 1-kestose comprising the steps of:

(a') concentrating a highly pure 1-kestose solution having 80% or more of 1-kestose to a Brix of at least 75, and heating the resultant concentrate to a temperature of at least 60° C., (b') concentrating the concentrate under a reduced pressure to lower the temperature of the concentrate and to initiate crystallization and allow the resultant crystals to grow, (c') heating the concentrate in accordance with step (c) of claim 1, and (d') repeating at least once steps (b) and (c) of claim 1, and recovering the crystal 1-kestose.

3. The process for producing crystal 1-kestose according to claim 1 or 2, wherein the concentrate having a Brix of 75 to 85 is concentrated under a reduced pressure.

4. The process for producing crystal 1-kestose according to claim 1 or 2, wherein the concentrate is concentrated in step (b) at an absolute pressure of 40 to 200 mmHg and a concentrate temperature of 40° C. to 70° C.

5. The process for producing crystal 1-kestose according to claim 1 or 2, wherein the concentrate is heated to 70° C. to 95° C. in step (c) to dissolve the microcrystals.

6. A process for producing crystal 1-kestose comprising the steps of:

($\alpha$') concentrating a highly pure 1-kestose solution having 80% or more of 1-kestose to a Brix of at least 80, maintaining the temperature of 50° C. to 60° C. to initiate crystallization, then maintaining the resultant crystals at 70° C. to 95° C. to grow the crystals, ($\beta$') cooling the concentrate by 5° C. to 20° C. from the temperature in step ($\alpha$'), ($\gamma$') maintaining the concentrate at the lowered temperature in step ($\beta$') to allow the crystals to grow, and ($\delta$') repeating at least once steps ($\beta$') and ($\gamma$'), lowering the temperature to 20° C. to 60° C., and recovering the crystal 1-kestose.

7. The process for producing crystal 1-kestose according to claim 6, wherein the 1-kestose solution in step ($\alpha$') has 90% or more of 1-kestose.

8. The process for producing crystal 1-kestose according to any one of claims 1, 2 or 6, wherein the 1-kestose solution in step (a), (a') or ($\alpha$') has a nystose content of 10% or less.

9. The process for producing crystal 1-kestose according to any one of claims 1 or 6, wherein the crystal 1-kestose is recovered at room temperature.

10. A continuous process for producing crystal 1-kestose comprising performing at least twice the process according to any one of claims 1, 2 or 6 to continually recover crystal 1-kestose from the 1-kestose solution.

11. A crystal 1-kestose obtained by the process according to any one of claims 1, 2 or 6, wherein the crystal 1-kestose is in the form of a columnar crystal having a length of 0.3 to 2 mm and a purity of at least 95%.

12. A crystal 1-kestose, in the form of a columnar crystal, having a length of more than 1.0 mm and a purity of at least 95%.

13. A crystal 1-kestose, in the form of a columnar crystal, having a length of more than 1.0 mm but not exceeding 1.2 mm and a purity of at least 95%.

14. The crystal 1-kestose according to claim 11, in the form of a columnar crystal, having a length of about 0.5 mm to 2 mm.

15. The crystal 1-kestose according to claim 11, in the form of a columnar crystal, having a length of about 1.0 mm to 1.2 mm.

16. The crystal 1-kestose according to claim 12, wherein the length of the crystal 1-kestose does not exceed 2.0 mm.

* * * * *